United States Patent
Speier et al.

(10) Patent No.: US 11,026,636 B2
(45) Date of Patent: Jun. 8, 2021

(54) METHOD FOR GENERATING A MEDICAL DATA SET OF A MOVING BODY PART

(71) Applicant: Siemens Healthcare GmbH, Erlangen (DE)

(72) Inventors: Peter Speier, Erlangen (DE); Mario Bacher, Nuremberg (DE); Michaela Schmidt, Uttenreuth (DE)

(73) Assignee: Siemens Healthcare GmbH, Erlangen (DE)

( * ) Notice: Subject to any disclaimer, the term of this patent is extended or adjusted under 35 U.S.C. 154(b) by 459 days.

(21) Appl. No.: 16/001,649

(22) Filed: Jun. 6, 2018

(65) Prior Publication Data
US 2018/0353139 A1 Dec. 13, 2018

(30) Foreign Application Priority Data

Jun. 8, 2017 (DE) .......................... 102017209708.6
Jul. 5, 2017 (EP) ...................................... 17179813

(51) Int. Cl.
*A61B 5/00* (2006.01)
*A61B 5/055* (2006.01)
(Continued)

(52) U.S. Cl.
CPC ........ *A61B 5/7285* (2013.01); *A61B 5/02444* (2013.01); *A61B 5/055* (2013.01);
(Continued)

(58) Field of Classification Search
CPC ... A61B 5/7285; A61B 5/7292; A61B 5/1107; A61B 5/02444; A61B 5/055;
(Continued)

(56) References Cited

U.S. PATENT DOCUMENTS

| 7,702,376 B2 | 4/2010 | Frank et al. |
| 7,899,521 B2 | 3/2011 | Demharter et al. |

(Continued)

FOREIGN PATENT DOCUMENTS

| DE | 102005051323 | 5/2007 |
| DE | 102015203385 | 8/2016 |
| DE | 102015224162 | 6/2017 |

OTHER PUBLICATIONS

Bonanno G. et al, Self-Gated Golden Angle Spiral CINE MRI for Endothelial Function Assessment, Proceedings of the International Society for Magnetic Resonance in Medicine, ISMRM, 25th Annual Meeting and Exhibition, Honolulu, Hawaii, USA, Apr. 22-27, 2017, No. 928, .pp. 928, XP040688496; 2017.

(Continued)

*Primary Examiner* — Peter Luong
(74) *Attorney, Agent, or Firm* — Lempia Summerfield Katz LLC

(57) ABSTRACT

A method is provided for generating a medical data set of a moving part of the human or animal body undergoing a cyclical movement such as cardiac movement. A raw data signal acquired by a magnetic resonance receiver coil arrangement is received. A magnetic resonance signal and a movement signal are separated from the raw data signal. At least two physiological phases of the moving body part are automatically assigned to the movement signal. The automatic assignment does not introduce a delay between the movement signal and the magnetic resonance signal. Time points used for triggering an acquisition of the magnetic resonance signal and/or for data post-processing of the magnetic resonance signal are determined or set.

20 Claims, 4 Drawing Sheets

(51) Int. Cl.
  *G01R 33/567* (2006.01)
  *G01R 33/563* (2006.01)
  *A61B 5/11* (2006.01)
  *A61B 5/024* (2006.01)
  *G01R 33/565* (2006.01)
  *A61B 5/352* (2021.01)

(52) U.S. Cl.
  CPC ............ *A61B 5/1107* (2013.01); *A61B 5/725* (2013.01); *A61B 5/7246* (2013.01); *A61B 5/7292* (2013.01); *G01R 33/5676* (2013.01); *G01R 33/56341* (2013.01); *A61B 5/0044* (2013.01); *A61B 5/352* (2021.01); *G01R 33/56509* (2013.01)

(58) Field of Classification Search
  CPC ..... A61B 5/7246; A61B 5/725; A61B 5/0044; A61B 5/0456; G01R 33/5676; G01R 33/56341; G01R 33/56509
  See application file for complete search history.

(56) References Cited

U.S. PATENT DOCUMENTS

| | | |
|---|---|---|
| 8,116,856 B2 | 2/2012 | Rβler |
| 2007/0106150 A1 | 5/2007 | Greiser et al. |
| 2016/0245888 A1 | 8/2016 | Bollenbeck et al. |
| 2017/0160364 A1 | 6/2017 | Fenchel et al. |
| 2017/0160367 A1* | 6/2017 | Schroter ............ G01R 33/3607 |

OTHER PUBLICATIONS

European Search Report cited in European Patent Application No. 17179813.5; Feb. 14, 2018; 13 pages.

I. Graesslin et al., Advancements in contact-free Respiration Monitoring using RF Pick-up coils, ISMRM 2010, Traditional Poster.; 2010; 1 page.

Nguyen, TD, et. al., Effective Motion-Sensitizing Magnetization Preparation for Black Blood Magnetic Resonance Imaging of the Heart, in: Journal of magnetic resonance imaging : JMRI. 2008; Vo. 28(5), pp. 1092-1100.

Pascal Spincemaille et al., Kalman filtering for real-time navigator processing, Magnetic Resonance in Medicine., vol. 60, No. 1, pp. 158-168, XP055447072, US ISSN: 0740-3194, DOI: 10.1002/mrm.21649; 2008.

Schroeder, L. et al., Novel Method for Contact-Free Cardiac Synchronization Using the Pilot Tone Navigator, in: proceedings of the 24th Annual Meeting of the ISMRM, Singapur, 7.-13.5.2016, pp. 410, 2016.

Tao Zhang et al, Robust self-navigated body MRI using dense coil arrays : Robust Self-Navigated Body MRI, Magnetic Resonance in Medicine, vol. 76, No. I, pp. 197-205; XP055447076, US ISSN: 0740-3194, DOI: 10.1002/mrm.25858; 2015.

Wetzl J. et al, Feasibility Study: Free-Breathing 3-D CINE Imaging with Respiratory Gating Based on Pilot Tone Navigation, Proceedings of the International Society for Magnetic Resonance in Medicine, ISMRM, 24th Annual Meeting and Exhibition, Singapore, May 7-13, 2016, No. 2613, pp. 2613, XP040683654,; 2016.

* cited by examiner

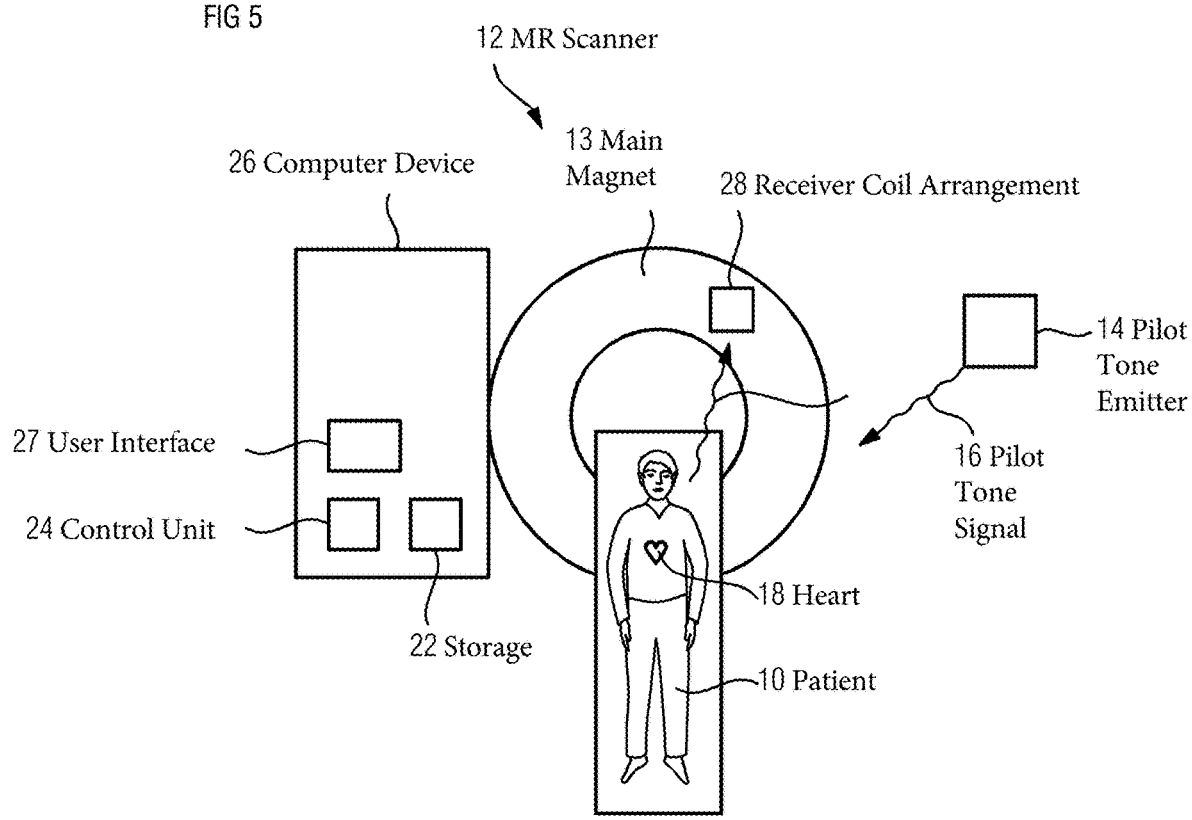

METHOD FOR GENERATING A MEDICAL DATA SET OF A MOVING BODY PART

CROSS REFERENCE TO RELATED APPLICATIONS

This application claims the benefit of DE102017209708.6 filed on Jun. 8, 2017 and EP17179813 filed on Jul. 5, 2017 both of which are incorporated by reference in their entirety.

FIELD

Embodiments provide a method for generating a medical data set of a moving body part, a computer program product, and a control unit.

BACKGROUND

Magnetic Resonance (MR) imaging is slow. Therefore, it is necessary to synchronize the data acquisition with any motion that affects the final image. An example is organ motion in the field-of-view (FOV). The motions for compliant patients include respiratory and cardiac motion. Cardiac motion generates pulsatile blood flow everywhere in the body. Applications that are sensitive to blood flow variations benefit or require synchronization to the cardiac motion even if the heart is far away from the FOV.

Cardiac synchronization may be achieved by monitoring the electric activity of the heart with an ECG (Electrocardiogram) device and deriving a trigger signal at the time of the R-wave, e.g., start of left-ventricular (LV) contraction. For example, documents U.S. Pat. No. 8,116,856 B2 or U.S. Pat. No. 7,899,521 B2 describe an arrangement for recording ECG signals and document U.S. Pat. No. 7,702,376 B2 describes a method for ECG-triggering a measuring sequence of a magnetic resonance device. The main advantages of the approach are that the R-wave is narrow and therefore the trigger time point may be well defined and appears at the start of the heart contraction. The disadvantages are that:

The ECG sensor must be attached to the patient requiring trained staff to place the electrodes after preparation of the skin of a patient with abrasive gels and in some cases shaving.

MR gradient switching induces currents in the Electrocardiography (ECG) leads that lead to artifacts in the measured signal that need to be suppressed.

In the strong magnetic field of the MR magnet, the ECG is superposed by another signal, generated by the hydromagneto-dynamic effect: blood contains ions that move with varying velocity in the magnetic field. The Lorenz force leads to a partial separation of positive and negative ions, generating macroscopic time varying net currents, that in turn induce currents in the ECG leads. The effect may be small on 1.5T-MRT-device. The effect increases with B0 and the surface covered by the ECG leads, so that the effect may become a problem at higher magnetic fields, e.g. 3T and 7T.

While two electrodes may be sufficient to detect an R-wave, multiple electrodes may be applied to increase ECG reliability. There may be, for example, four electrodes in use. From the electrodes, a spatial direction of electrical activity is derived (vector ECG). The direction follows a time course that depends on the electrode geometry relative to the heart, and therefore on the orientation of the patient. The time course is learned and applied as a detection filter to suppress non-ECG signals. Unfortunately, depending on the patient, the heart moves more or less with respiratory motion and therefore the time course will vary more or less with the respiratory state, that reduces reliability of the ECG during deep breathing. In some patients, the heart rate decreases after inspiration in breath-holding, leading to impaired image quality.

One technique for inferring information about respiratory motion or patient motion during patient acquisitions in MR measurements, termed "Pilot Tone (PT) Navigation" has been described in DE 10 2015 203 385 A1 and further in post-published document DE 10 2015 224 162 A1, that is incorporated herein by reference.

The principle is to measure the variation induced by physiological motion by a coherent and/or continuous external frequency signal received by the local coil elements outside the receive bandwidth of the actually scanned MR field of view, but within the range of the oversampling bandwidth that is acquired during every readout. The resulting movement signal, referred to as the Pilot Tone signal or cardiac component or cardiac component trace, includes a different shape than the ECG signal, and may not feature a prominent R-wave. Extracting suitable time points for synchronization therefore presents new challenges and provides unique opportunities that require ways to extract the information.

SUMMARY

The scope of the present invention is defined solely by the appended claims and is not affected to any degree by the statements within this summary. The present embodiments may obviate one or more of the drawbacks or limitations in the related art.

Embodiments provide a method for MR-acquisition that uses the Pilot Tone signal and that provides synchronization of the MR acquisition with the cardiac motion.

The Pilot Tone (PT) stands out as a simple and low-cost extension to an MR system/scanner that includes negligible hardware cost, since the PT is using most of the existing hardware (MR receive and processing facilities, and potentially signal generation facilities), and is constrained by the MR system's parameters, notably MR operating frequency, receiver bandwidth and maximal signal amplitude. The PT features more receiving channels than other methods (in a MR setup between 16 and 40 channels) distributed around the imaged volume of approx. diameter 50 cm.

When comparing the different alternatives, the PT system may be used for cardiac motion state detection, for example, Pilot Tone contact-free cardiac synchronization, that was first described in Schroeder, L., Wetzl, J., Maier, A., Lauer, L., Bollenbeck, J., Fenchel, M., Speier, P. A "*Novel Method for Contact-Free Cardiac Synchronization Using the Pilot Tone Navigator*", Proceedings of the 24th Annual Meeting of the ISMRM, Singapur, 7.-13.5.2016, pp. 410, 2016.

Pilot Tone acquisition provides cardiac and respiratory synchronization based on PT signals, that are robust against setup variations and variations in patient physiology. The multiple features of the cardiac component of the PT signal, that follows the cardiac contraction cycle, provide synchronization of the sequence to arbitrary cardiac phases, instead of synchronization to a single time point only (R-wave peak in the case of ECG).

Further embodiments are directed to how various clinically desirable applications may be improved or realized using the ability to synchronize the measurement or aspects of it to arbitrary cardiac phases.

The applications are distinguished between: Real time applications that detect the cardiac phase based on the PT in real-time and modify the execution of the sequence (e.g., trigger or gate), and retrospective applications where a time interval of PT-CC is analyzed during or after the measurement, and the results of the analysis are used to parametrize subsequent measurements, or for image reconstruction or post processing of the magnetic resonance signal from the analysis or other time intervals. The analysis may, for example be carried out on a special calibration measurement and applied to parametrize a subsequent clinical magnetic resonance scan, or the analysis may be carried out on one scan and the results applied to guide the image reconstruction or post-processing of the same scan.

A method is carried out—either in real-time or retrospectively—on a raw data signal acquired by a magnetic resonance receiver coil arrangement during a magnetic resonance scan. An MR-scan is an acquisition of magnetic resonance spectroscopy or imaging data from a human or animal, usually a patient, for example, from a moving part of the human or animal body (body part). The body part may be the heart or any other organ affected by motion, such as a blood vessel, thorax or lung, or more distal body parts, that are affected by the pulsatile arterial blood flow.

At least a portion of the body part may be undergoing or may be affected by a cyclical movement, e.g. cardiac movement. The method may be carried out during the complete magnetic resonance scan but may also be limited only to one or several stages or time intervals of the scan.

A raw data signal acquired by a magnetic resonance receiver coil arrangement is received, for example, from a clinical MR-scanner. The receiver coil arrangement may be a standard MR local coil including several channels, for example, in the form of a coil array. Each channel acquires a separate signal component. The raw data signal includes several, possibly complex, signal components. The receiver coil arrangement may have 4-128 or 8-64, receiver channels.

The raw data signal may be received, and the method carried out inline, e.g. on a control unit or computer associated with the MR scanner. Especially for retrospective applications, the method may also be carried out offline, e.g. on a remote server or computer available via a network connection.

The magnetic resonance signal and the movement signal (e.g. the Pilot Tone signal) are separated from the raw data signal. The movement signal is derived from and/or describes the mechanical activity of the moving body part, in contrast to ECG, that is derived from the electrical activity. The PT signal is modulated by the movement of the body part since the movement influences the signal transmission between the source of the Pilot Tone signal and the receiver coil arrangement.

Once the Pilot Tone signal is separated from the raw data signal based on the frequency content, the movement signal relating to the cardiac movement (also called PT-CC for "Pilot Tone Cardiac Component") is separated from the other Pilot Tone signal components. Principal component analysis (PCA) or independent component analysis (ICA) may be used. In an embodiment, a demixing matrix W separating the cardiac component from the other components is calculated from a short calibration scan. Once the demixing matrix has been calculated, the matrix is applied to the incoming Pilot Tone signal to furnish the desired movement signal, e.g. the cardiac component.

In a next act, at least two physiological phases of the moving body part are assigned to the movement signal. The automatic assignment does not introduce a delay between the movement signal and the medical scan signal. A physiological phase may be a phase in the cyclical movement, such as mid-diastole, end-diastole, etc. The term "physiological phase" may also indicate a particular time point or point of interest within the cyclical cardiac movement, such as the start and end of the mid-diastolic phase. The assignment may be done continuously, not just on the signal from one cardiac cycle. At least two physiological phases may be assigned per cardiac cycle, e.g. end-systole and end-diastole.

The automatic assignment of the physiological phases may be done by applying an adaptive or stochastic or model-based filter to the movement signal, as will be described in more detail below.

The act provides automatic determination and/or setting of time points used for triggering an acquisition of the magnetic resonance signal (in real-time applications and/or for data-post processing the magnetic resonance signal (in retrospective applications). The automatic determination may be based on template and/or model-based feature detection within the movement signal, as will be described in more detail below. For real time applications, the last two acts may be carried out continuously with no delay during the whole or part of the acquisition of the raw data signal. For post-processing applications, the last two acts are also carried out for the whole or part of the movement signal, but not necessarily in real time.

Thus, the time points used for triggering or post-processing may be selected at any arbitrary physiological phase or point of interest in the movement signal. For example, it is possible to select points of interest, that may not be possible with ECG triggering based on R-wave detection, e.g. because the points of interest are points shortly before the R-wave, or the points of interest are simply too remote from the R-wave to be reliably implemented in an arrhythmic heart, or the points of interest may be identified using additional cine imaging scans only.

The time points for triggering may be transmitted to the MR scanner or a control unit, to be used during the MR acquisition. The time points used for post-processing may be used on an offline server.

Embodiments provide reliable ECG-free cardiac imaging. In comparison with known ECG-based imaging methods, embodiments may be implemented at lower costs. Further, since no leads have to be attached to the patient, there is better patient comfort and the preparation time for the radiological examination is reduced. In addition, the method is more reliable than ECG because there is no interference between the Pilot Tone signal and the MR signal, and thus provides increased triggering reliability.

Embodiments may reliably extract the desired time points also from patients with severe arrhythmia since the physiological phases are automatically assigned to the movement signal (e.g. the cardiac component). The automatic assignment of the physiological phases (e.g. cardiac phases) to the movement signal may be performed by applying an adaptive or stochastic or model-based filter to the movement signal, for example, the cardiac component of the movement signal.

Contrary to ECG-based triggering, embodiments provide a synchronization of the scan of medical data to arbitrary cardiac phases, also in arrhythmic hearts.

The physiological phases may include at least one of the following phases or points of interest in the cardiac movement: diastole, systole, mid-diastolic phase, mid-systolic phase and—systole, and—diastole, start and end of the mid-systolic phase, start and end of the mid-diastolic phase.

The filter may fulfil the following criteria: If the filtered movement signal is to be used in triggering, the filter may not introduce significant delay. Therefore, advanced filters like adaptive or stochastic or model-based filters may be necessary.

The filter may not only suppress noise of the cardiac component but may also provide information about the relevant physiological phases, thus allowing automatic determination of trigger points. Since the movement signal is obtained by a completely different mechanism than an ECG signal, the movement signal does not have the distinctive R-wave, that may easily be used as trigger point. Rather, the movement signal may be analyzed to determine the physiological phases.

In an embodiment, the adaptive or stochastic or model-based filter is first trained or adapted to the cardiac component, for example, to the cardiac component derived from a calibration portion. Alternatively, the filter adapts during the processing of the raw data signal acquired by the MR receiver coil arrangement, e.g. during the actual method.

The adaptive or stochastic or model-based filter often relies on an a priori model of the cardiac cycle in either the time and/or frequency domain. Model based filtering is robust against measurement noise and provides triggering on any, arbitrary points in the cardiac cycle. In the absence of severe arrhythmia, model-based methods may also be able to predict cardiac activity beyond the current state. Therefore, model-based or stochastic filters may be applied to the movement signal.

The filter may be a Kalman Filter, or an Extended Kalman filter, or is a Switched/Switching Kalman Filter. The Switching Kalman Filter switches between several models during various phases of the cyclical movement. Kalman filtering, also known as linear quadratic estimation (LQE), is an algorithm that uses a series of measurements observed over time, containing statistical noise and other inaccuracies, and produces estimates of unknown variables that tend to be more accurate than those based on a single measurement alone, by using Bayesian inference and estimating a joint probability distribution over the variables for each timeframe. The Kalman filter provides, on the basis of the past measurements, e.g. the calibration portion, for each filtered data point of the movement signal, a probably correct data point. The switched Kalman filter may also include information on the physiological phase of the data point, e.g. may already assign the physiological phase. The Kalman, Extended Kalman and Switched/Switching Kalman filter make us of prior information trained on actual data. Thus, the filters and other model-based filters make use of a model of the movement signal.

The underlying model for implementations using the (Extended) Kalman Filter/Smoother may be generated either in the frequency and/or time domain. Once such a model has been generated, e.g. by analysis of the cardiac component acquired during the calibration phase, segmentation may be achieved by various methods, such as Hidden Markov Models or Switched Kalman Filters. The methods may also be used retrospectively to obtain segmentations of the cardiac component.

In an embodiment, the adaptive or stochastic or model-based filter uses a model that incorporates physiological information about the cyclic movement, for example, the cardiac movement. The model may be based on a preconfigured model, that may however be configured to the actual movement signal received during the scan of medical data, such as a Hidden Markov Model.

"Automatically assigning" implies that the assignment is performed without user input and may be done by the filter operation as described above. The filters may identify sections or points of interest of the movement signal and allocate the physiological phases of the cyclical movement to the identified sections or points of interest.

In real-time applications, the act of assigning the physiological phases may be performed such that no delay is introduced between the movement signal and the magnetic resonance signal acquired at the same time as the movement signal. The term "no delay" implies that the delay may be kept to a minimum, for example, between 0-10 ms and for example less than 1 ms, so that the time points used for triggering are effectively generated in real time. Hence, the time points may be used for triggering the MR scan in which the raw data signal including the MR data is acquired.

When no real-time functionality is needed, forward-backward filtering using either FIR or IIR digital filters in the time-domain or frequency-domain filtering on the cardiac component may be used to generate a filtered movement signal, on which feature detection algorithms (such as the above-described adaptive or stochastic or model-based filters) may be applied to assign the physiological phases. "Forward-backward filtering" is a filter method that provides that the filtered movement signal is not shifted in time by the filter, so there is no delay between the images acquired during the scan of medical image data and the movement signal derived from the Pilot Tone signal (even if the images are not processed in real time).

In a next act, the time points used for triggering the acquisition of the magnetic resonance signal and/or for data post-processing of the magnetic resonance signal are automatically determined and/or set. The time points may be extracted from the, e.g. filtered, movement signal.

The determination may be done by template- or model-based feature detection, that may already be part of the filtering with a stochastic or adaptive or model-based filter such as the Kalman filter, as described above. Alternatively, the movement signal (e.g. the cardiac component) may first be filtered for denoising and then analyzed.

For example, the first and/or second derivative of the (filtered) movement signal is calculated and automatically analyzed to extract time points used for triggering or post-processing.

Possible useful trigger points are: max (abs (1st derivative))=max velocity or max (abs (2nd derivative))=max acceleration or the minimum/maximum of the cardiac component trace. The points are easily obtained from the smoothed cardiac component and correspond to interesting features in the cardiac cycle like the early systolic and diastolic phases. Trigger points approximating the ECGs R-peak may be obtained by threshold-based triggering using the mid-diastolic amplitude as an indicator.

In an embodiment, a user may first define physiological phases or points of interest, at which the time points are to be set in the movement signal. Alternatively, the user only selects the type of MR-examination desired and the control unit of the MR-scanner automatically determines at which physiological phase or point of interest triggers are required. Then, acquisition of the magnetic resonance signal and movement signal starts, and the selected phases or points of interest are automatically extracted from the movement signal by the acts described above.

When time points are defined by a user, it may be practical to first display the cardiac component to the user, for example by showing the movement signal, averaged over several cardiac cycles, for the length of one or two cycles. The user may then set the desired time points by a user interface including e.g. a mouse, touch-screen, etc. Once the points are thus defined, the points are extracted automatically from the incoming movement signal.

In an embodiment, the movement signal reflects the heart beat and the time points are determined independently from the R-wave and/or other electrical activity of the heart. The movement signal is the cardiac component of the Pilot Tone signal. The Pilot Tone is not affected by electrical activity of the heart, but reflects the actual movement occurring in the volume near the Pilot Tone emitter and the receiver coil elements. During Brain imaging, the Pilot Tone emitter may be placed on the chest and a chest coil arrangement is using only for Pilot Tone acquisition, while the head coil channels are used for imaging.

Embodiments of cardiac real-time applications are provided.

The methods are based on the minimal (or no) delay in the processing of the movement signal, and template feature detection. Besides arbitrary user-defined points, one may use:

Minima and maxima of the cardiac component, max(abs(1st derivative))=max velocity, max(abs(2nd derivative))=max acceleration Any assignment of physiological phases (event flagging) based on the detected feature will take into account the processing delay.

In an embodiment, at least one time point for triggering is automatically set in the R-R interval preceding the cardiac cycle during which the corresponding magnetic resonance signal is acquired, that is not possible with ECG triggering, that naturally does not allow a trigger shortly before the R-wave. The setting is useful for the acquisition of magnetic resonance signals from the systolic phase that require a long preparation period (e.g., inversion pulse and subsequent wait time), and therefore at least one time point for triggering a preparation pulse is automatically set during the diastolic phase preceding the systolic phase. When the moving body part is the heart, magnetic resonance data may be acquired in the systolic state, because the myocardium is thicker in systole, that simplifies the analysis (e.g. reduced contamination of blood pool). Further, for patients with fast heart rates and pediatric patients, the silent period of the heart is often longer in systole than in diastole. In the embodiment, a "long" preparation period means long by MR-sequence standards, such as 20-400 ms.

Examples for the embodiment (systolic acquisition) including preparation pulses in the preceding diastolic phase) are:

Example 1

Stable myocardial Late Gadolinium Enhancement (LGE) magnetic resonance imaging. LGE is based on the delayed wash-in and wash-out of Gd-containing contrast agent in myocardial tissue affected by infarction. The increased amount of Gd in the extracellular space in the infarcted tissue may be demonstrated by T1-weighted imaging in a time period of 10-30 minutes after contrast administration. The techniques used for LGE-imaging in end-systole may require an inversion recovery (IR) pulse, that is played out in the previous R-cycle, since the inversion time is fixed by the MR imaging protocol. Thus, if LGE-imaging during systole is desired, the IR-pulse must be triggered in the preceding cardiac cycle.

Example 2

T1 mapping in systole. For the evaluation of the heart, for example to evaluate infarction, it is crucial to have as many pixels in myocardium as possible (transmural), but without including blood pool or air, that might lead to big errors. A larger diameter of the myocardium, as may be seen in the state of maximum ventricular contraction, is therefore an advantage. However, T1-mapping again requires a long preparation period, e.g. an inversion recovery or saturation pulse followed by a predetermined inversion time. Thus, if the data readout is to take place during systole, it is advantageous to be able to play out the inversion pulse out in the previous RR-cycle.

Example 3

STIR-imaging. In STIR-imaging (Short TI Inversion Recovery), the fat signal is inverted, and the signal is read out when fat crosses zero. To perform STIR at systole, also the required inversion pulse might need to be played out before the ECG-trigger time point at the R-wave, thus in the end-diastolic phase.

According to an embodiment, the time points used for triggering are used to optimize a MOLLI-type measurement. "MOLLI" stands for "Modified Look-Locker Imaging". The basic strategy is to use only 2-3 inversion pulses followed by several single-shot b-SSFP (balanced steady-state-free precession) read-outs at various fixed inversion times. Short rest periods are interspersed to allow recovery of longitudinal magnetization between cycles. In conjunction with parallel imaging and conjugate symmetry methods, MOLLI allows accurate T1-values of myocardium to be obtained in only one breath-hold per slice.

MOLLI and other cardiac T1 quantification types (sh-MOLLI, SASHA, etc.) require a series of images to be acquired at the same cardiac phase, but with varying inversion time. The signal evolution may be characterized if the TI values are well distributed without bunching, e.g. spaced evenly, or with smoothly varying distances. However, the presently used ECG triggering on the R-wave limits the variations possible. Triggering on an arbitrary phase allows to place the inversion pulse without restrictions and thus allows realization of an optimal distribution of TI points. Thus, MOLLI-type measurements with evenly distributed T1 points are possible.

According to further embodiments, a time point used for triggering a preparation pulse is moved along the cardiac cycle for different repetitions of the magnetic resonance sequence, or for the acquisition of different sub-sections of k-space allowing for optimization of the contrast in cardiac MR-imaging, e.g. since it allows to acquire the central sub-section of k-space during periods of optimal contrast, and outer portions during periods of less ideal contrast as described in DE 10 2005 051 323 A1. Further, a contrast may be stabilized for the central portion of k-space while full coverage of cardiac cycle is generated. The advantage of using the Pilot Tone over the ECG is that time points are relative to the heart motion, not relative to the R-wave, thus more stable in case of changing heart rate or arrhythmia As an example, the embodiment may be applied to contrast-prepared CINE-images. CINE images are short movies that are able to show heart motion throughout the cardiac cycle. In previous techniques, CINE images were obtained with ECG triggered segmented imaging. Segmented acquisition is the process of dividing the cardiac cycle into multiple segments (frames) to produce a series of images that may be displayed as a movie (CINE). Each image in the CINE may be composed of information gathered over several heart beats allowing for a movie to be acquired in a breath-hold of 10-20 s depending on the sequence. As in any movie, the final CINE is a sequence of individual frames.

The MR sequence may for example be an inversion or saturation prepared CINEAST, tagging or DENSE imaging. In such sequences with a preparation pulse, contrast varies across the cardiac cycle as the magnetization preparation fades into the readout steady state. Optimal contrast may occur directly after preparation or a certain time after preparation. The resulting contrast may be stabilized along the cardiac cycle by moving the preparation along the cardiac cycle for different repetitions of the sequence or during acquisition of different sub-sections of k-Space and combining the resulting data intelligently. An approach is to acquire after preparation only one or a few phases of the cardiac cycle. Other approaches acquire central k-Space during periods of optimal contrast and outer portions during periods of less ideal contrast. The method, e.g. Pilot Tone triggering, provides for moving the start of the sequence or the preparation pulse not only to different phases of the cardiac cycle but also to the preceding RR interval and thus allows to fill gaps in the existing applications, like the early systolic phase in tagging or IR prepared cine. By removing the limitation, longer and thus more effective or elaborate preparations may be used without loss of coverage of the cardiac cycle.

According to another embodiment, the sequence may use multiple trigger time points simultaneously: one to prepare the contrast, and one to start and stop the acquisition, or two separate acquisitions targeting different cardiac phases. Thus, several time points per cardiac cycle may be extracted from the movement signal and used to control different events in a sequence.

According to another embodiment, a time point used for triggering is set on the onset of the mid-diastolic phase for acquiring an image data set of the end diastolic state. The embodiment provides robust acquisition of end diastolic images in the presence of heart rate variations. While the time (after R-wave) of the end-systolic phase is quite independent of heart rate, the time of mid-diastolic phase scales with the heart rate in a patient-specific fashion. Therefore, segmented high resolution diastolic images may become blurred when the heart rate varies during acquisition. By triggering directly on the onset of the mid-diastolic phase the positioning of the acquisition window and thus the image quality may be stabilized for most applications.

According to another embodiment, the movement signal is analyzed for a characterization of arrhythmic heart beats, for example, to reject the magnetic resonance signal acquired during an arrhythmic heartbeat. Based on shape similarity measures, heartbeats may be categorized and processed separately; in an implementation, data belonging to some categories may be rejected. The embodiment may be performed in real-time but may be a retrospective application as well.

Embodiments may be performed as retrospective applications but may be real-time applications as well. For retrospective applications, the movement signal (the cardiac component of the Pilot Tone signal) may be stored together with the magnetic resonance signal and exported together with the DICOM data to support post processing. For delay-free offline processing, a delay-free filtering method, such as forward/backward-filtering, may be used. On the filtered movement signal, a template-based feature detection may be performed to assign the physiological phases of the moving body part to the movement signal, and for determining the time points used for data post-processing.

For training the filter or for deriving a model for the template-based feature detection, data of the current or a previous scan may be used, in which raw data was acquired, for example, a special Pilot Tone calibration scan or a previous scan of the MR-exam, e.g. a localizer scan.

According to an embodiment, the time points for data post-processing or for triggering are set at distinct motion states, for example at end-systolic and/or end-diastolic time points. The time points may indicate maximum and minimum contraction of the heart and may allow very interesting image processing, e.g. when a scaling of a time axis is required (see below). The time points may be used as input for inline or offline post-processing of the acquired magnetic resonance signal.

According to an embodiment, the time points are set at time points of average strain to place strain-sensitive measurements there, for example diffusion measurements. The points may be found under the assumption that the relationship between strain and signal modulation of the cardiac component of the PT (e.g. the movement signal) is linear: The time points of average strain correspond to the time points where the PT-CC assumes its time averaged value (averaged over a cardiac cycle).

According to an embodiment, the time points are set at optimal time points for motion sensitive dark blood preparation, for example at time points of maximum slope in the movement signal (i.e. at maximum velocity) or of maximum second order derivative of the movement signal (i.e. at maximum acceleration). The configuration is useful for the Dark Blood technique using flow-based blood suppression, e.g. described in Nguyen TD, de Rochefort L, Spincemaille P, et al. Effective Motion-Sensitizing Magnetization Preparation for Black Blood Magnetic Resonance Imaging of the Heart. Journal of magnetic resonance imaging: JMRI. 2008; 28(5):1092-1100. doi:10.1002/jmri.21568. MR black blood techniques are therefore suitable to segment myocardium from the blood pool. The preparation pulses may be placed within the cardiac cycle, for example motion sensitized preparation blocks may be placed on time points of maximum slope in the cardiac component, corresponding to maximum contraction velocity of the myocardium, for M1 sensitized modules. Alternatively, the preparation may be triggered by time points corresponding to maxima of the second derivative of the cardiac component for acceleration sensitive modules.

According to an embodiment, the time points are used for positioning acquisition windows to specific time periods, for example to silent periods in a cardiac interval. For static MR measurements, the organ may not move significantly during the acquisition to avoid artifacts or blurring. For cardiac imaging, acquisitions may be limited to windows of negligible cardiac motion, such as end-systolic phase, mid- and end-diastolic phase.

According to an embodiment, the time points for data post-processing are used for matching the time resolution of retro-gated CINE images. The frames may be retrospectively distributed, or the time resolution changed, to match the time resolution to each cycle and to the physiology to avoid under-estimation of cardiac activity. The principle is as follows:

To reduce scan time, cardiac phase time resolution is on the order of 35-50 ms. If the end-systolic phase falls in the middle of a reconstructed frame, the maximum contraction is most optimally characterized. If end-systolic phase is distributed across two frames, the contraction is underestimated. The positions of reconstructed frames for retro-gated CINEs may be freely selected during reconstruction. If the frames are placed according to the position of the end-systolic phase as determined by the method from the PT-CC data (the cardiac component of the Pilot Tone signal), then underestimation of the cardiac contraction is minimized. The embodiment may be performed in real-time as well.

According to an embodiment, time points for triggering or data post-processing of a magnetic resonance signal acquired across multiple heart beats are set according to features of the movement signal or models thereof, allowing for the extraction of such features from the PT-CC signal. For example, when the time points are set along a time axis, a non-linear scaling of the time axis may be performed when the heart rate changes during the acquisition. Combining images or segmented k-Space data measured across multiple heart beats require scaling the time axis if the heart rate changes during the acquisition. The scaling may be non-uniform (e.g. a duration of systole stays nearly constant, diastole stretches) and patient specific. Image quality may be optimized, if the interpolation rule is derived from previous scans or the same scan and is applied during reconstruction or assembly of the data. The relevant features of the cardiac movement may be extracted from the movement signal, and the time points may be scaled in an optimized manner in each cardiac cycle.

BRIEF DESCRIPTION OF THE FIGURES

FIG. 5 depicts an MR-scanner in a schematic view according to an embodiment.

DETAILED DESCRIPTION

In the following and with reference to FIG. 1, a Pilot Tone signal is acquired during an MR scan. The processing of the acquired raw data signal may include the following acts:

Calibration: The calibration may be the same as described in the DE 10 2015 224 162 A1. The purpose of the calibration is to determine the frequency of the Pilot Tone signal and to separate the magnetic resonance imaging signal from the additional Pilot Tone signal.

Pre-processing: Optionally Down-sampling the Pilot Tone signal (including several signal components from the several receiving coil channels) and optionally low-pass filtering or bandpass filtering to suppress unwanted signals, such as the respiratory signal, and normalizing the phases of all channels to a reference phase.

Processing: Calculating a demixing matrix W separating the cardiac component by applying an independent component analysis (ICA), for example from a short calibration scan and applying the demixing matrix on incoming data.

Filtering/triggering: For real-time applications, denoising of the cardiac component and feature detection to enable triggering on an arbitrarily positioned predefined points in the cardiac cycle.

Filtering/post-processing: For retrospective applications, retrospective processing of the cardiac component and the feature extraction.

Visualization: Optionally, real-time visualization of the filtered movement signal, e.g. the processed cardiac component.

Figure 1:
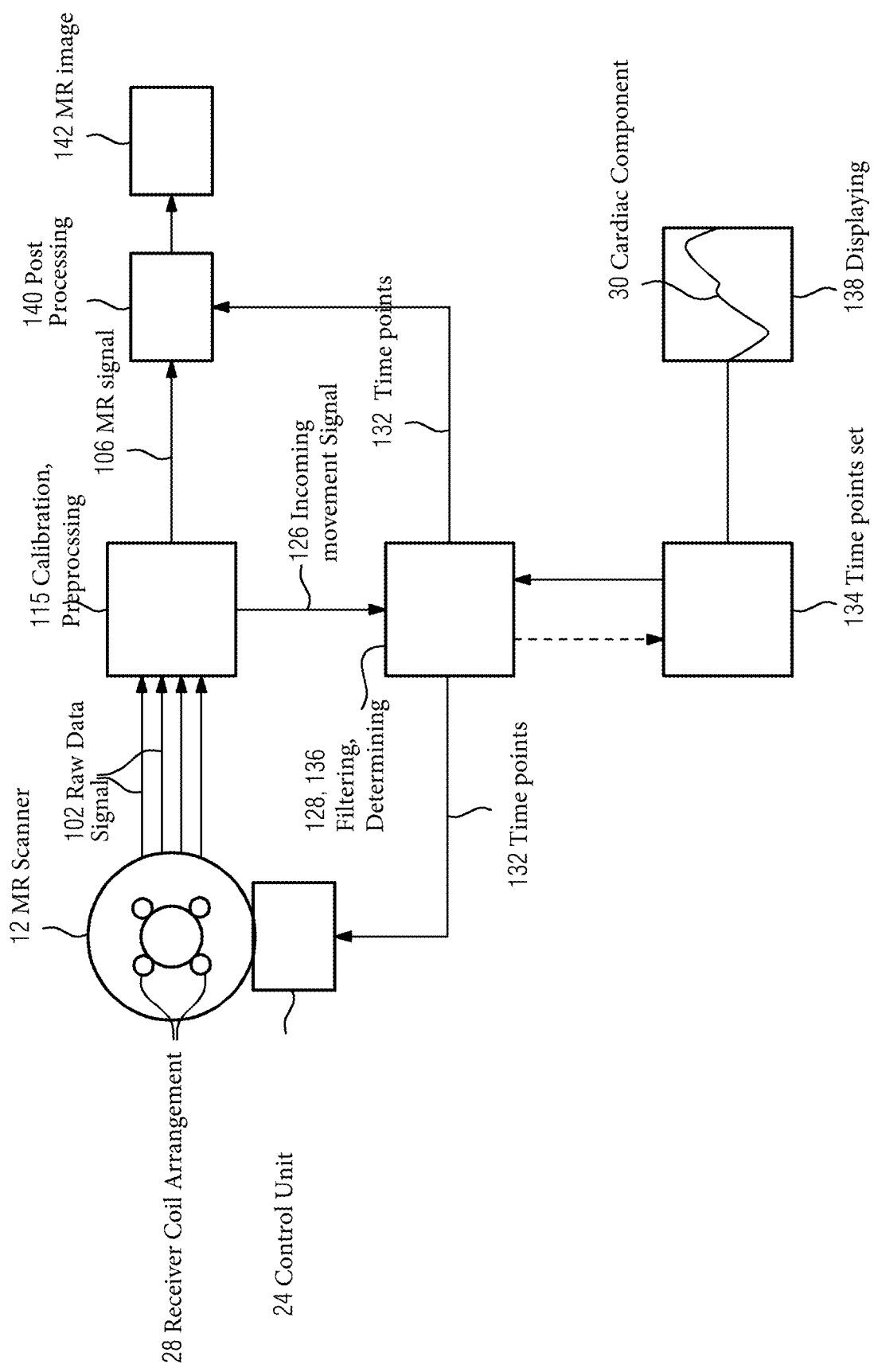
FIG. 1 depicts a schematic flow diagram of an embodiment.

FIG. 1 centers, for example, on the filtering. The MR scanner 12 including a receiver coil arrangement 28 with (in the schematic example) four coils/channels is depicted on the top left. When the acquisition starts, the receiver coil arrangement acquires a raw data signal 102 including 4 signal components, from which the magnetic resonance signal 106 and the movement signal 126, namely the cardiac component of the Pilot Tone signal, are separated in act 115. Act 115 also includes the calibration, pre-processing and processing.

The movement signal 126 is then subjected to filtering 128 as described above, that includes the automatic assigning of the physiological phases to cardiac component 126. In an embodiment, the filter may first be trained on a calibration portion of the movement signal. Since the filter takes some time to converge, using calibration data a priori speeds up conversion for the actual scan. However, in other applications, the filter 128 adapts over time to the incoming movement signal 126 and does not require a calibration.

Figure 2:
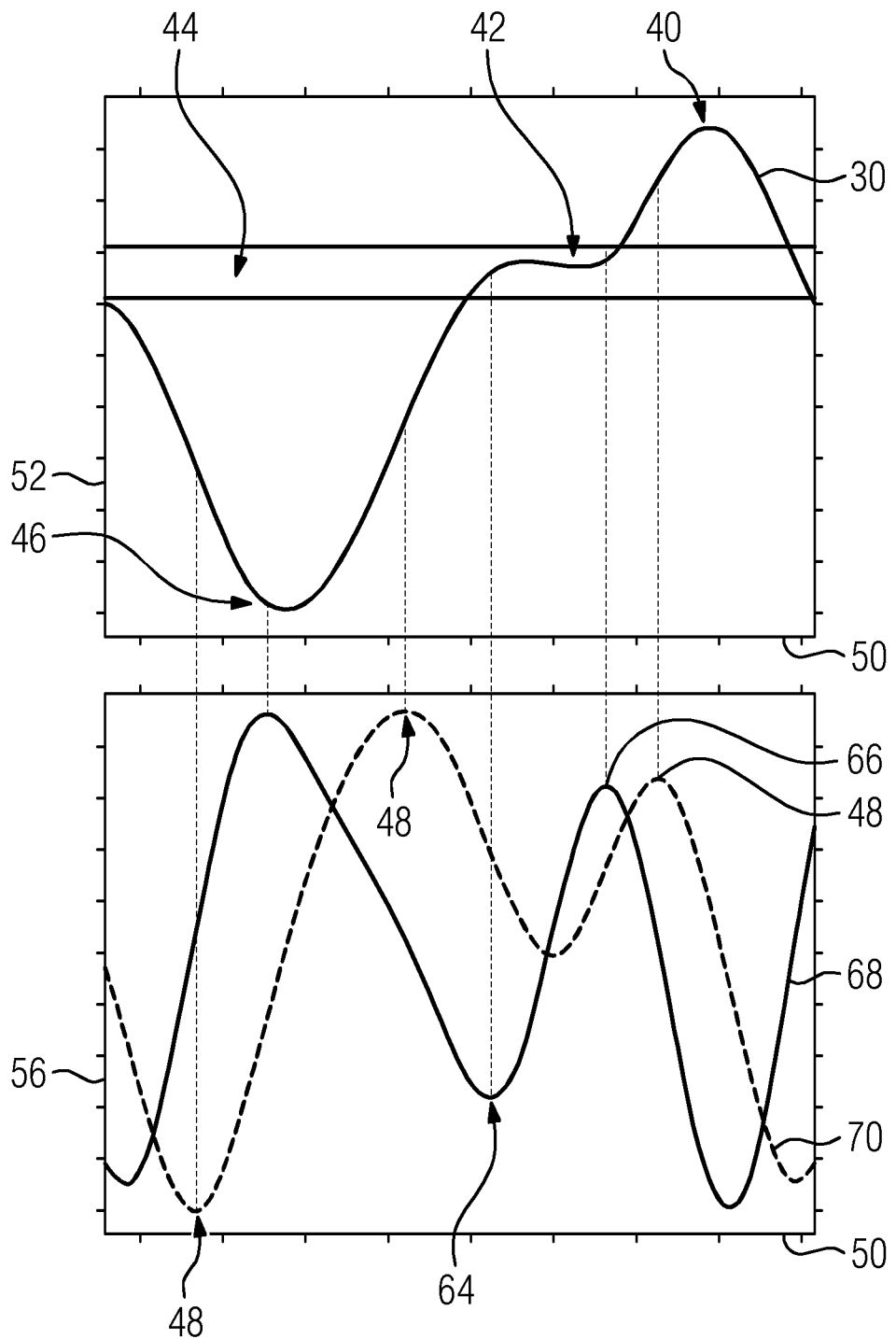
FIG. 2 depicts an example of a cardiac component over one cardiac cycle and a 1st and 2nd derivative.

Some physiological phases that may be assigned to the cardiac component are depicted in FIG. 2 described below.

Returning to FIG. 1, at the same time or after the filtering 128, time points 132 for triggering or post-processing may be automatically set in the filtered movement signal or may be set automatically by the filter. As described above, an adaptive or stochastic or model-based filter may be able to adapt a model of the movement signal so that each incoming data point is automatically fitted to the model and thus its physiological phase, for example its position with the cardiac cycle, is identified. The acts 128/136 may be performed continuously and in real time on the incoming movement signal 126.

Optionally, the physiological phases or points of interest where the time points are to be set are selected in an act 134. Act 134 may be inherent in the selection of the MR protocol used for the acquisition of the raw data signal 102, or act 134 may require user interaction. The movement signal 30 may be displayed on a screen 138 and the user selects arbitrary time points within the cardiac cycle. Alternatively, the user describes the desired time points, such as "Maximum of first derivative". The information is passed on and used in act 136 in the determination of the time points 132.

Thus, time points 132 to be used for triggering or post-processing are continuously generated. In real time applications, the time points for triggering are fed to the control unit 24 of the MR scanner 12 and used in the acquisition of the raw data signal, for example of the magnetic resonance signal. Alternatively, or additionally, in retrospective applications, time points 132 are also extracted and are used in a post-processing 140 of the magnetic resonance signal 106. From the post-processing, a magnetic resonance image 142 may result.

The movement signal may be filtered in act 128 as described above, e.g. by a switched Kalman filter based on a model generated by analysis of the cardiac component acquired during a calibration phase. The filtered movement signal, e.g. the cardiac component 30, is depicted in the top graph of FIG. 2, in a plot of amplitude 52 in arbitrary units versus time 50. In the bottom part of the graph, the first derivative 70 (in dashed line) and second derivative 68 of the filtered movement signal/cardiac component are also shown in arbitrary units 56 plotted against time 50. From the filtered cardiac component trace, the following points of interest may be derived: The minimum of the cardiac component trace 46 indicates systole, e.g. the maximum contraction and resting phase. The maximum of the cardiac component phase 40 indicates end-diastole, e.g. the physiological phase of maximum expansion of the heart during the resting phase. The plateau 42 may be associated with the mid-diastolic phase, in which the ventricle is relaxed, e.g. a resting phase. The area 44 indicates the signal level for R wave occurrence and may be used in a threshold trigger. The minima and maxima of the first derivative 70 of the cardiac component indicate the times of maximum velocity. The minimum 64 and the maximum 66 of the second derivative 58 indicate the start and end of the mid-diastolic phase.

Figure 3:
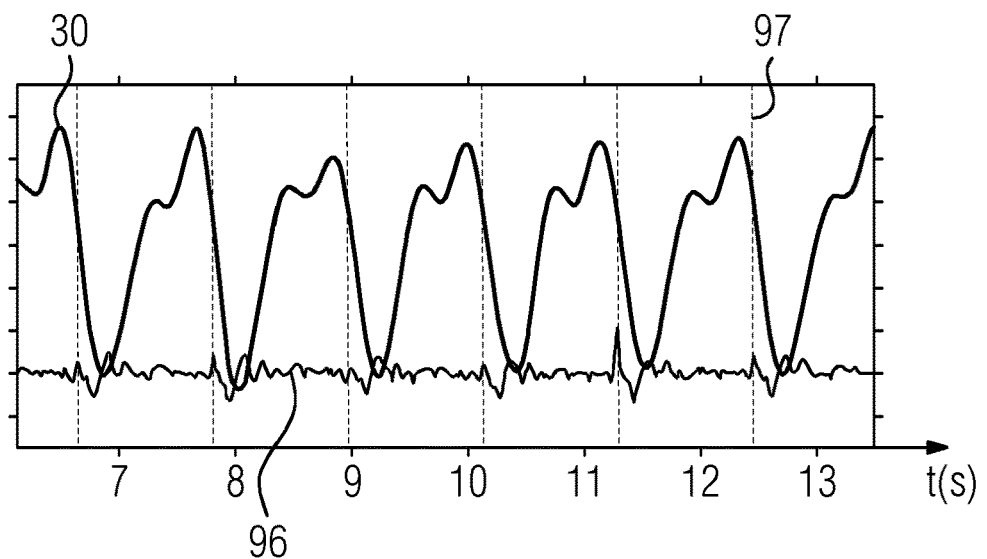
FIG. 3 depicts a schematic Bandpass-filtered cardiac component trace and corresponding ECG trace according to an embodiment.

FIG. 3 is a depiction of visualization. In FIG. 3, the cardiac component trace 30 is plotted over six cardiac cycles against time. The cardiac component trace 30 is depicted over a time span of about 7 seconds. The cardiac component trace 30 includes been band-pass filtered before. A corresponding ECG trace 96 is also plotted, where the respective R waves are shown as dashed lines 97.

Figure 4:
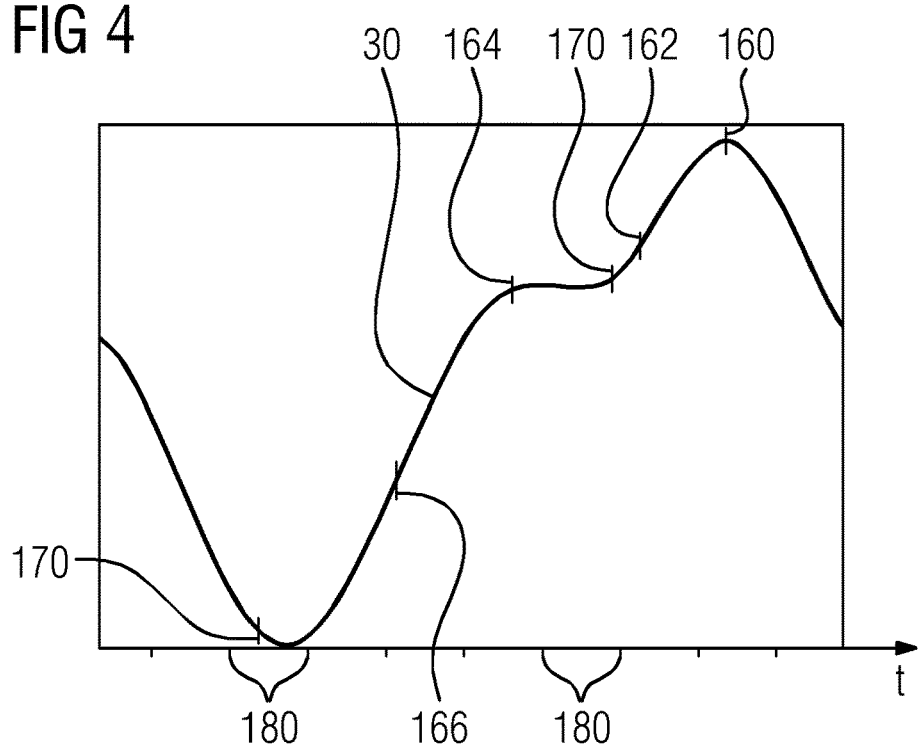
FIG. 4 depicts an example of a cardiac component over one cardiac cycle, and relevant trigger points.

FIG. 4 depicts an example of a filtered cardiac component 30 over one R-R interval, and various time points that may be determined/set. For example, 160 indicates a trigger point at end-diastole, that may be used for a preparation pulse for acquiring an image such as LGE in the systolic phase of the next R-R cycle (not shown). Time points 162, 164 and 166 illustrate how trigger points, e.g. for triggering a preparation pulse, are moved along the cardiac cycle for different repetitions of an MR sequence. Thereby, the contrast may be optimized, as described above.

Time points 170 illustrate time points of maximum second order derivative of the movement signal, i.e. time points of maximum acceleration. The time points may be useful in dark blood imaging.

Further, the cardiac component 30 may be divided into frames to be used in CINE imaging, by a number of time points 180 distributed over the cardiac cycle. In retro-gated CINEs, it the time resolution may be matched to the individual cardiac cycle. Thus, by selecting the position of the time points 180 according to their physiological phase, and not according to a pre-determined time resolution, image quality may be improved. For example, one trigger point 180 may be set so that the end-systolic phase falls into one frame. The sequence of time points 180 may be distributed not in constant time intervals, but each position in each cycle may be adapted to the physiological phases in that particular cardiac cycle.

FIG. 5 depicts a schematic MR scanner 12. The MR-scanner 12 includes a main magnet 13 and a control unit 24, by which the data acquisition of the MR scanner 12 may be controlled. The control unit 24 may be part of a computer device 26. The computer device may also include a digital storage medium 22 and a User interface 27 including e.g. a display, a keyboard, mouse, touch screen, etc. A patient 10 may be examined, for example to perform MR imaging of the heart 18.

To provide the movement signal, a pilot tone signal 16 is emitted by a pilot tone emitter 14, that may be a separate RF source. The pilot tone emitter 14 is positioned close to the heart, e.g. strapped to the local coil 28 or included in the coil. In FIG. 5, the pilot tone emitter 14 is depicted within the bore of the main magnet 13. The pilot tone signal is modulated by the movement of the heart 18 and the lung (not shown).

The (modulated) pilot tone signal is received by the receiver coil arrangement 28, that may be a local coil 28, such as a head coil or chest array coil, but may also be the body coil.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for generating a magnetic resonance image of a moving body part that is undergoing a movement cycle, the method comprising:
    receiving a raw data signal acquired by a magnetic resonance receiver coil arrangement;
    separating a magnetic resonance signal and a movement signal from the raw data signal, wherein the movement signal is derived from, describes, or is derived from and describes a mechanical activity of the moving body part within the movement cycle, wherein the movement signal is a cardiac component of a Pilot Tone signal;
    automatically assigning at least two physiological phases of the moving body part to the movement signal, wherein the automatic assignment does not introduce a delay between the movement signal and the magnetic resonance signal; and
    automatically determining, setting, or determining and setting one or more time points for triggering an acquisition of the magnetic resonance signal, for processing of an acquired magnetic resonance signal, or for triggering the acquisition of the magnetic resonance signal and for processing of the acquired magnetic resonance signal;
    generating the magnetic resonance image using the one or more time points and the acquired magnetic resonance signal, the processed acquired magnetic resonance signal, or the acquired magnetic resonance signal and the processed acquired magnetic resonance signal.

2. The method of claim 1, wherein the automatic determination is based on template-based feature detection, model-based feature detection, or template-based feature detection and model-based feature detection within the movement signal.

3. The method of claim 1, wherein a first derivative, a second derivative, or the first derivative and second derivative of the movement signal are provided and used in the automatic determining, setting, or determining and setting of the one or more time points.

4. The method of claim 1, further comprising:
    defining, prior to the automatic determining, a physiological phase or a point of interest at which the one or more time points are to be set in the movement signal.

5. The method of claim 1, wherein the one or more time points are determined at any arbitrary physiological phase or point of interest in the movement signal.

6. The method of claim 1, wherein at least one time point for triggering of the one or more time points is automatically set in an R-R interval preceding a cardiac cycle during which a corresponding magnetic resonance signal is acquired.

7. The method of claim 6, wherein the acquisition of the magnetic resonance signal requires a long preparation period, and at least one time point for triggering a preparation pulse is automatically set during a diastolic phase preceding a systolic state.

8. The method of claim 7, wherein the at least one time point for triggering a preparation pulse is moved along the cardiac cycle for different repetitions of magnetic resonance sequence, or for an acquisition of different sub-sections of k-Space.

9. The method of claim 1, wherein the one or more time points for processing are set at an end-systolic point, or an end-diastolic time point, or the end-systolic point and the end-diastolic time point.

10. The method of claim 1, wherein the one or more time points are set at time points of average strain in order to place strain sensitive measurements at the time points of average strain.

11. The method of claim 10, wherein the strain sensitive measurements are diffusion measurements.

12. The method of claim 1, wherein the one or more time points are set at optimal time points for motion sensitive dark blood preparation.

13. The method of claim 12, wherein the optimal time points for motion sensitive dark blood preparation are time points of maximum slope in the movement signal or of maximum second order derivative of the movement signal.

14. The method of claim 1, wherein the one or more time points for processing are used for matching a time resolution of retro-gated cinematic or cine images such that underestimation of cardiac activity is avoided.

15. The method of claim 1, wherein the one or more time points for triggering or processing of magnetic resonance signal acquired across multiple heart beats are set according to features of the movement signal.

16. A non-transitory computer-readable storage medium storing instructions executable by a controller to generate an image of a moving part of a human undergoing a cardiac movement, the instructions comprising:
receiving a raw data signal acquired by a magnetic resonance receiver coil arrangement;
separating a magnetic resonance signal and a movement signal from the raw data signal, wherein the movement signal is derived from and describes a mechanical activity of the moving part within a movement cycle, wherein the movement signal is a cardiac component of a Pilot Tone signal;
automatically assigning at least two physiological phases of the moving part to the movement signal, wherein the automatic assignment does not introduce a delay between the movement signal and the magnetic resonance signal;
automatically determining time points for triggering an acquisition of the magnetic resonance signal for processing of the magnetic resonance signal, or for triggering the acquisition and processing of the magnetic resonance signal; and
automatically generating the image using the time points and the acquired magnetic resonance signal, the processed acquired magnetic resonance signal, or the acquired magnetic resonance signal and the processed acquired magnetic resonance signal.

17. The non-transitory computer-readable storage medium of claim 16, wherein the automatic determination is based on template-based feature detection, model-based feature detection, or template-based feature detection and model-based feature detection within the movement signal.

18. The non-transitory computer-readable storage medium of claim 16, wherein a first derivative, a second derivative, or the first derivative and the second derivative of the movement signal is provided and used in the automatic determination of the one or more time points.

19. The non-transitory computer-readable storage medium of claim 16, wherein at least one time point for triggering of the one or more time points is automatically set in an R-R interval preceding a cardiac cycle during which a corresponding magnetic resonance signal is acquired.

20. An apparatus for generating an image of a moving part of a human undergoing a cardiac movement, the apparatus comprising:
a magnetic resonance scanner configured to acquire a raw data signal;
a computer device associated with the magnetic resonance scanner, the computer device configured to:
separate a magnetic resonance signal and a movement signal from the raw data signal, wherein the movement signal is derived from and describes a mechanical activity of the moving part within a movement cycle, and wherein the movement signal is a cardiac component of a Pilot Tone signal;
automatically assign at least two physiological phases of the moving part to the movement signal, wherein the automatic assignment does not introduce a delay between the movement signal and the magnetic resonance signal;
automatically determine, set, or determine and set one or more time points for triggering an acquisition of the magnetic resonance signal, for processing of the magnetic resonance signal, or for triggering the acquisition of the magnetic resonance signal and for processing of the magnetic resonance signal; and
automatically generate the image using the one or more time points and the acquired magnetic resonance signal or the processed acquired magnetic resonance signal.

* * * * *